United States Patent [19]

Bredehorst et al.

[11] Patent Number: 5,705,634

[45] Date of Patent: Jan. 6, 1998

[54] HIGH YIELD PREPARATION OF DIMERIC TO DECAMERIC CHITIN OLIGOMERS

[75] Inventors: Reinhard Bredehorst, Hamburg, Germany; Nicholas Pomato, Frederick, Md.; Oliver Scheel, Pinneberg; Joachim Thiem, Hamburg, both of Germany

[73] Assignee: PerImmune Holdings, Inc., Rockville, Md.

[21] Appl. No.: 397,464

[22] Filed: Mar. 2, 1995

[51] Int. Cl.$^6$ .............................. C08B 37/08; C08B 37/00
[52] U.S. Cl. ........................... 536/124; 536/18.5; 536/20; 536/123.1; 127/34
[58] Field of Search .......................... 536/18.5, 123.1, 536/20, 124; 127/34

[56] References Cited

U.S. PATENT DOCUMENTS

| | | | |
|---|---|---|---|
| 3,922,260 | 11/1975 | Peniston et al. | 536/20 |
| 4,286,087 | 8/1981 | Austin et al. | 536/20 |
| 4,804,750 | 2/1989 | Nishimura et al. | 536/20 |
| 4,929,722 | 5/1990 | Partain et al. | 536/20 |
| 5,053,113 | 10/1991 | Krepets et al. | 205/689 |

FOREIGN PATENT DOCUMENTS

| | | |
|---|---|---|
| 0 226 452 | 6/1987 | European Pat. Off. |
| 2701030 | 8/1994 | France |
| 2261802 | 10/1990 | Japan |
| 03002203 | 1/1991 | Japan |
| 3234702 | 10/1991 | Japan |
| 319607 | 11/1971 | U.S.S.R. |
| 1571047 | 6/1990 | U.S.S.R. |

OTHER PUBLICATIONS

Bough et al. *Mar. Ext. Serv. (Univ. of GA)*, vol. 20(12): 1931–1943, (1978) Month Not Available.

K. Suzuki et al., "Antitumor effect of hexa-N-acetylchitohexaose and chito-hexaose," *Carbohydrate Research*, 151:403–408 (1986) Month Not Available.

D. Roby et al., *J. Biochim. Biophys. Res. Comm.*, 143:885–892 (1987) Month Not Available.

S.A. Barker et al., "Amino-sugars and related compounds," *J. Chem. Soc.*, 451:2218–2227, 1958 Month Not Available.

J.A. Rupley, "The hydrolysis of chitin by concentrated hydrochloric acid, and the preparation of low molecular-weight substrates for lysozyme," *Biochim. Biophys. Acta*, 83:245–255 (1964) Month Not Available.

M.A. Raferty et al., "Separation of glycosaminoglycan saccharide and glycoside mixtures by gel filtration," *Analytical Biochemistry*, 30:427–435 1969 Month Not Available.

B. Capon et al., "The preparation of chitin oligosaccharides," *J. Chem. Soc.*, (C) 1654–1655, 1970 Month Not Available.

C. Bosso et al., "The behavior of chitin towards anhydrous hydrogen fluoride Preparation of β-(1-4)-linked 2-acetmido-2-deoxy-D-glucopyranosyl oligosaccharides," *Carbohydrate Research*, 156:57–68, 1986.

H. Hashimoto et al., "Synthesis of chitooligosaccharide derivatives by condensation polymerization," *J. Carbohydrate Chemistry*, 8(2):307–311 (1989) Month Not Available.

T. Usui et al., "Enzymic synthesis of useful chito-oligosaccharides utilizing transglycosylation of chitinolytic enzymes in a buffer containing ammonium sulfate," *Carbohydrate Research*, 203:65–77, 1990 Month Not Available.

M. Akaboshi et al., "Preparation of 2-acetamido-2-deoxy-β-D-glucose oligosaccharides from acid hydrolyzates of chitin by electrolytic desalting and exclusion chromotography," *Anal. Biochem.* 46:687–689, 1972 Month Not Available.

M. Izume et al., "Preparation of N-acetylchitooligosaccharides from enzymatic hydrozylates of chitosan," *Biosci. Biotech. Biochem.*, 56(8) 1327–1328 (1992) Month Not Available.

*Primary Examiner*—John Kight
*Assistant Examiner*—Howard C. Lee
*Attorney, Agent, or Firm*—Mary E. Gormley; William M. Blackstone

[57] ABSTRACT

The present invention is directed to a new process for the production of chitin oligomers, including fragmentation, partial hydrolysis and recovery. This process produces high yields, especially of higher (tetra- to deca-) chitin oligomers.

56 Claims, 9 Drawing Sheets m = 0 Di-N-acetyl-chitobiose m = 1 Tri-N-acetyl-chitotriose m = 2 Tetra-N-acetyl-chitotetraose m = 3 Penta-N-acetyl-chitopentaose m = 4 Hexa-N-acetyl-chitohexaose m = 5 Hepta-N-acetyl-chitoheptaose m = 6 Octa-N-acetyl-chitooctaose m = 7 Nona-N-acetyl-chitononaose m = 8 Deca-N-acetyl-chitodecaose

| Neutralized Chitin Hydrolysate | Volume [ml] | Sodium Chloride [g] |
|---|---|---|
| Before Electrodialysis | 1,500 | 292.2 |
| After Electrodialysis | 1,350 | < 0.1 |

FIG. 5

| Chitin-Oligomer | Yield [g/100 g chitin] | Elution Time on Biogel P4 [min] | m/z (M+H) |
|---|---|---|---|
| $(GlcNAc)_2$ | 8.6 | 685 | 425 |
| $(GlcNAc)_3$ | 8.9 | 650 | 628 |
| $(GlcNAc)_4$ | 8.7 | 610 | 831 |
| $(GlcNAc)_5$ | 8.1 | 505 | 1034 |
| $(GlcNAc)_6$ | 3.6 | 465 | 1237 |
| $(GlcNAc)_7$ | 1.0 | 430 | 1440 |
| $(GlcNAc)_8$ | 0.3 | 405 | 1643 |
| $(GlcNAc)_9$ | 0.2 | 385 | 1846 |
| $(GlcNAc)_{10}$ | 0.3 | 360 | 2049 |

FIG. 7

| Neutralized Chitin Hydrolysate | Volume [ml] | Sodium Chloride [g] |
|---|---|---|
| Before Flow Filtration | 1,500 | 292.2 |
| After Flow Filtration | 750 | 151.9 |

FIG. 9

HIGH YIELD PREPARATION OF DIMERIC TO DECAMERIC CHITIN OLIGOMERS

FIELD OF THE INVENTION

The present invention is directed to new processes for producing high yields of chitin oligomers, which are useful inter alia as antitumor agents and for eliciting chitinase in plants.

BACKGROUND OF THE INVENTION

There is growing evidence of the biological activities of water-soluble chitin oligomers. For example, hexa-N-acetyl-chitohexaose and hepta-N-acetyl-chitoheptaose have shown significant antitumor activity against Sarcoma 180 solid tumors in Balb/c mice (Suzuki, K., Mikami, T., Okawa, Y., Tokoro, A., Suzuki, S., and Suzuki, M. Carbohydr. Res. 151: 403–408, 1986). Furthermore, hexa-N-acetyl-chitohexaose and hepta-N-acetyl-chitoheptaose are efficient elicitors of chitinase activity in melon plants (Roby, D., Gadelle, A., and Toppan, A. Biochim. Biophys., Res. Commun. 143: 885–892, 1987). Based on these and other results, chitin oligomers, especially higher chitin oligomers, are promising oligosaccharides with the potential of various useful biological activities.

Known methods for obtaining higher chitin oligomers, however, give either low (in some cases poor) yields of higher chitin oligomers, employ too time-consuming purification methods, or are not suitable for large scale production.

Barker, S. A., Foster, A. B., Stacey, M., and Webber, J. M. (J. Chem. Soc. 2218–2227, 1958) teach how to obtain chitin oligomers by acetolysis of chitin and subsequent de-O-acetylation. As stated by the authors, however, the low overall yields of higher chitin oligomers and tedious isolation procedures largely deprive the acetolysis method of preparative value.

Rupley, J. A. (Biochim. Biophys., Acta 83: 245–255, 1964) teaches how to obtain chitin oligomers by hydrolysis of chitin in concentrated hydrochloric acid. Chitin oligomers up to penta-N-acetyl-chitopentaose are obtained after purification of the neutralized chitin hydrolysate on a charcoal-Celite column. The yields of tetra-N-acetyl-chitotetraose and penta-N-acetyl-chitopentaose, however, are very low. Dimeric and trimeric chitin oligomers are the predominant species.

Raferty, M. A., Rand-Meir, T., Dahlquist, F. W., Parsons, S. M., Borders, Jr., C. L., Wolcott, R. G., Beranek, Jr., W., and Jao, L. (Anal. Biochem. 30: 427–435, 1969) teach how to obtain chitin oligomers up to hexa-N-acetyl-chitohexaose by using the hydrolysis procedure described by Rupley, J. A. (Biochim. Biophys., Acta 83: 245–255, 1964), but using a Bio-Gel P-2 gel filtration column for purification of the neutralized chitin hydrolysate. However, the yield of hexa-N-acetyl-chitohexaose (1.3 g/100 g chitin) is still low.

Capon, B., and Foster, R. L. (J. Chem. Soc. 1654–1655, 1970) report even lower yields of hexa-N-acetyl-chitohexaose (0.13 g/100 g chitin) after hydrolysis of chitin in concentrated hydrochloric acid as described by Rupley, J. A. (Biochim. Biophys., Acta 83: 245–255, 1964) and subsequent purification of the desalted chitin hydrolysate on a Sephadex LH 20 column.

Nishimura, T., Eto, E., and Yamada, T. (European Patent Application EP 0 226 452 A3, 1986) teach how to improve the yields of hexa-N-acetyl-chitohexaose significantly by additional irradiation with ultrasonic waves during the processes of i) mixing finely ground chitin with concentrated hydrochloric acid and ii) subsequent acid hydrolysis of the dispersed chitin particles. This method, however, does not provide for hepta-N-acetyl-chitoheptaose and higher chitin oligomers. Furthermore, desalting of neutralized chitin hydrolysates is performed by gel filtration on Sephadex G-25 columns, a tedious and time-consuming purification step due to the large volumes of neutralized chitin hydrolysates.

Bosso, C., Defaye, J., Domard, A., Gadelle, A., and Pedersen, C. (Carbohydr. Res. 156: 57–68, 1986) teach how to produce chitin oligosaccharides by fluorohydrolysis of chitin in anhydrous hydrogen fluoride. By purification of fluorohydrolysis samples of chitin on Bio-Gel P-4 gel filtration columns dimeric to decameric chitin oligomers are obtained in good yields. Hydrogen fluoride fluorohydrolysis of chitin, however, suffers from the fact that this method is not suitable for the production of chitin oligomers on an industrial scale.

Hashimoto, H., Abe, Y., Horito, S., and Yoshimura, J. (J.Carbohydr. Chem. 8: 307–311, 1989) teach how to synthesize chitin oligomers by oligomerization of a thioglycoside having a free hydroxyl group. Chitin oligomers up to undecamers are formed by this procedure as confirmed by HPLC analysis of the reaction mixture. The method, however, is only suitable for the production of small quantities of chitin oligomers for analytical purposes.

In a different approach, Usui, T., Matsui, H., and Isobe, K. (Carbohydr. Res. 203: 65–77, 1990) teach how to synthesize chitin oligomers from di-N-acetyl-chitobiose by lysozyme-mediated transglycosylation reactions or from tetra-N-acetyl-chitotetraose by chitinase-mediated transglycosylation reactions. The addition of ammonium sulfate to the reaction systems results in an increased production of hexa-N-acetyl-chitohexaose and hepata-N-acetyl-chitoheptaose due to their poor solubility in salt-containing solutions. Most of the hexameric and heptameric chitin oligomers precipitate during the reaction, thereby withdrawing these oligomers from the competing hydrolytic actions of lysozyme and chitinase. The quantities of hexa-N-acetyl-chitohexaose and hepta-N-acetyl-chitoheptaose obtained by this methodology, however, do not exceed the lower milligram range. Therefore, this enzymatic approach is also not suitable for large scale production of higher chitin oligomers.

As evident from the foregoing description of known procedures for the production of higher chitin oligomers, there is a need for a new method that i) allows the rapid production of higher chitin oligomers, preferably hexameric to decameric chitin-oligomers, in high yields, and ii) is suitable for the production of chitin oligomers on an industrial scale. It is the objective of the present invention to overcome the limitations of known procedures and to provide a method for the production of chitin oligomers that satisfies the aforementioned requirements.

SUMMARY OF THE INVENTION

One object of this invention is to provide a method for rapid production of water-soluble dimeric to decameric chitin oligomers, especially tetra-N-acetyl-chitotetraose, penta-N-acetyl-chitopentaose, hexa-N-acetyl-chitohexaose, hepta-N-acetyl-chitoheptaose, octa-N-acetyl-chitooctaose, nona-N-acetyl-chitononaose, and deca-N-acetyl-chitodecaose in high yields. The structure of these chitin oligomers is shown in FIG. 1. Another objective of the invention is to provide a method that is suitable for the production of large quantities of chitin oligomers on an industrial scale.

In one embodiment, the invention comprises a four-step method (method A) for the production of dimeric to decameric chitin oligomers in high yields. The first step of the procedure is the fragmentation of chitin to superfine particles using a hammer mill equipped with a combination of one or more beater systems (e.g., double-sided swing beaters) and special grinding tracks (e.g., baffle-ribbed grinding tracks). This special milling technique allows the production of particles, within a few minutes, with a mean diameter of less than about 120 μm. The chitin particles are dissolved in concentrated hydrochloric acid and subjected to partial hydrolysis. Hydrolysis is stopped by neutralization, preferably with sodium hydroxide, and the reaction mixture is desalted by electrodialysis, a technique which allows almost complete desalination of chitin oligomers within a short period of time. Hydrolysis is controlled to produce dimeric to decameric oligomers. Hydrolysis is preferably controlled to produce pentameric to decameric oligomers. In the last step, the desalinated chitin hydrolysate is subjected to a separation procedure, e.g., gel filtration on a polyacrylamide Bio-Gel P-4 column. All steps of method A are adaptable to an industrial scale.

In another embodiment, the invention comprises a four-step method (method B) for the predominant production of tetrameric to heptameric chitin oligomers. Method B represents a modified version of method A, in which flow filtration is used for desalination instead of electrodialysis. While flow filtration techniques require more time for desalination than electrodialysis, low molecular weight cut-off flow filtration membranes allow for a simultaneous removal of non-desired N-acetylglucosamine, dimeric and trimeric chitin oligomers. All steps of method B are also adjustable to an industrial scale.

The invention also comprises a combination of methods A and B in that flow filtration techniques may be used after desalination of neutralized chitin hydrolysates by electrodialysis. Such a combination allows the removal of N-acetylglucosamine, dimeric and trimeric chitin oligomers from the chitin hydrolysate prior to column chromatography, and, thereby, increases the percentage of the desired higher chitin oligomers in the sample.

BRIEF DESCRIPTION OF THE FIGURES

FIG. 5. Effect of electrodialysis on volume and sodium chloride content of neutralized chitin hydrolysates. Experimental details are described in Example 3.

FIG. 7. Yields and characteristics of dimeric to decameric chitin oligomers obtained by method A.

FIG. 9. Effect of tangential flow filtration on volume and sodium chloride content of neutralized chitin hydrolysates. Experimental details are described in Example 4.

DESCRIPTION OF THE PREFERRED EMBODIMENTS

Figure 1:
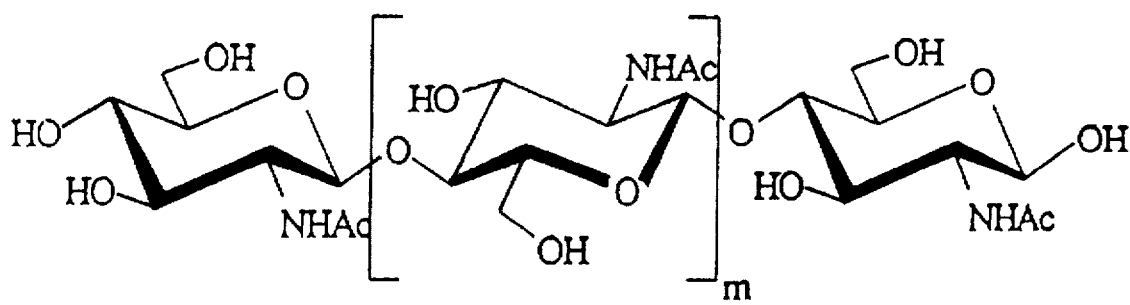
FIG. 1. Structures of dimeric to decameric chitin oligomers.

Preferred methods for the production of water-soluble chitin oligomers (di-N-acetyl-chitobiose, tri-N-acetyl-chiotriose, tetra-N-acetyl-chitotetraose, penta-N-acetyl-chitopentaose, hexa-N-acetyl-chitohexaose, hepta-N-acetyl-chitoheptaose, octa-N-acetyl-chitooctaose, nona-N-acetyl-chitononaose, and deca-N-acetyl-chitodecaose) include four- and five-step procedures. The five-step procedure represents a refinement of the four-step procedures.

In one preferred embodiment, a procedure for the production of water-soluble dimeric to decameric chitin oligomers (method A) is comprised of the following four steps:

(I) fragmentation of chitin to superfine particles with a mean diameter of 120 μm or less;

(II) partial hydrolysis of the fragmented chitin in a concentrated hydrohalogenic acid;

(III) desalination of neutralized chitin hydrolysates by electrodialysis; and (IV) separation of desalted chitin oligomers, e.g., by Bio-Gel P-4 gel filtration.

The chitin which is used as starting material in the preferred embodiment of this invention is a naturally occurring material composed of β-1,4-linked polysaccharides of N-acetylglucosamine. Chitin is available in large quantities, for example from the outer shells of Crustacea such as crabs and lobsters, from the shells of insects, and from the cell walls of a variety of microorganisms. A preferred starting material is a purified or partially purified product of chitin.

It is known that chitin is insoluble in water, organic solvents, and aqueous alkali metal hydroxide solutions. It is also known that finely ground chitin can be dissolved in concentrated HCl, or any concentrated hydrohalogenic acid. Rupley, J. A. (Biochim. Biophys.. Acta 83: 245–255, 1964) teaches how to powder chitin by 48 hour grinding in a ball mill. Using this method, however, the solubility of ground chitin in concentrated HCl is very limited (about 20 mg/ml). In a preferred embodiment of step I of the present invention, chitin is fragmented to superfine particles by treatment with a hammer mill equipped with a double-sided swing beater system and a baffle-ribbed grinding track (e.g., Multi-Purpose Mill 25 MZ, Hosokawa Alpine AG, Augsburg, Germany). Using this novel procedure, within a few minutes (100 g chitin requires less than 5 minutes) chitin particles are produced with a diameter of 120 μm or less. This super-finely ground material is readily soluble in concentrated HCl at a concentration of 200–400 mg/ml (at least 10-fold higher than Rupley, supra). Similar hammer mills equipped with flat steel beaters, strip steel beaters, or hammer beam beaters or a combination thereof are available for the fragmentation of chitin on an industrial scale (e.g., Omniplex Hammer Mills, Hosokawa Alpine AG, Augsburg, Germany). In another preferred embodiment of step I, chitin particles with a diameter of 120 µm or less are further fragmented to particles with a diameter of 10–50 µm by treatment with a fine impact mill equipped with a combination of stud discs, plate beaters, beater discs, shearing discs, and cutting knives as grinding elements (e.g., Fine Impact Mill 100 UPZ-II, Hosokawa Alpine AG, Augsburg, Germany). Similar fine impact mills are available for the fragmentation of chitin on an industrial scale (e.g., UPZ Fine Impact Mills, Hosokawa Alpine AG, Augsburg, Germany). Alternatively, a zigzag classifier may be used to cut chitin particles with a diameter of 120 µm or less to particles with a diameter of 10–50 µm (e.g., Zigzag Classifier 1–40 MZM, Hosokawa Alpine AG, Augsburg, Germany). In still another embodiment of step I, chitin particles with a diameter of 10–50 µm are further fragmented to ultra-small particles with a diameter of less than 10 µm by treatment with an air-stream ultrafine classifier (e.g., Turboplex Ultrafine Classifier 50 ATP, Hosokawa Alpine AG, Augsburg, Germany). The same principle can be used for the fragmentation of chitin to particles with a diameter of less than 10 µm on an industrial scale (e.g., Turboplex Ultrafine Classifiers ATP-GS or ATP-S/GS, Hosokawa Alpine AG, Augsburg, Germany).

In a preferred embodiment of step II, partial hydrolysis of fragmented chitin is performed in concentrated hydrochloric acid. Rupley, J. A. (Biochim. Biophys.. Acta 83: 245–255, 1964), incorporated herein by reference, teaches how to dissolve powdered chitin in concentrated hydrochloric acid, and how to generate water-soluble dimeric to pentameric chitin oligomers by acid hydrolysis of dissolved chitin. He teaches in detail the effects of temperature and concentration of hydrochloric acid on the kinetics of the hydrolysis process and the yields of individual chitin oligomers. In one aspect of the preferred embodiment of step II, chitin particles are dissolved in 12.5M hydrochloric acid. The concentration of chitin is preferably in the range of 0.2–0.4 g/ml, and most preferably 0.25 g/ml. The hydrolysis is preferably carried out at a temperature of 20°–45° C. most preferably at 40° C. for a period of 100 to 150 minutes. During the process of hydrolysis the reaction mixture is continuously agitated by means of a mechanical stirrer. In another aspect of the embodiment of step II, chitin hydrolysates are neutralized with aqueous sodium or potassium hydroxide after completion of the hydrolyzing reaction. Prior to the addition of aqueous sodium or potassium hydroxide, the chitin hydrolysates are cooled to low temperatures (about 4° C.) in a water bath containing an ice/salt mixture. The sodium or potassium hydroxide solution, preferably 50% and ice-cold, is added to the cooled chitin hydrolysates under conditions that allow the temperature of the reaction mixture to be kept always below about 25° C. During the process of neutralization, the reaction mixture is continuously agitated by means of a mechanical stirrer. In another aspect of the embodiment of step II, the neutralized reaction mixtures are filtered or centrifuged to remove insoluble material. The insoluble material is washed, dried and weighed to determine the degree of hydrolysis of chitin.

In a preferred embodiment of step III, neutralized reaction mixtures are desalted by electrodialysis. Akaboshi, M., Kawai, K., and Waki, A. (Anal. Biochem. 46: 687–689, 1972) teach how to desalinate a mixture of N-acetylglucosamine and dimeric to pentameric chitin oligomers by an electrolytic procedure. Their method, however, is extremely time-consuming since desalination of 2 liters of a neutralized chitin hydrolysate requires a period of 40 hours.

In a preferred embodiment of step III of the present invention, a significantly improved electrodialysis procedure is used for the desalination of neutralized chitin hydrolysates. With this technique, high salt concentrations can be decreased to less than 0.1 g/l within a short period of time. Complete desalination of 3-fold larger volumes (6 liters) of neutralized chitin hydrolysates to a level of sodium chloride that is below the detection level with silver nitrate, requires only six to seven hours. Furthermore, the period of time required for desalination can be easily decreased by one order of magnitude or more if the membrane surface (e.g. number of membranes in the stacks) is increased accordingly. Since electrodialysis processes allow an almost unlimited up-scaling, this desalination procedure is especially suited for industrial purposes. Electrodialysis systems useful for step III contain a diluate circuit, a concentrate circuit and an optional electrode rinsing circuit. The diluate is depleted of ions (desalted), the concentrate is enriched with ions (concentrated), and the electrode rinsing circuit is designed to protect the electrodes. Each circuit is closed. The diluate flows into the cell stack, consisting of alternating cation and anion-exchange membranes. In the cell stack, the ions migrate towards the counterpole of the applied field. The ions permeate the membranes, thereby migrating from the diluate to the concentrate circuit. The subsequent membranes prevent ion migration from continuing, anion-exchange membranes provide a barrier for cations and cation-exchange membranes provide a barrier for anions. Thus, the electrolytically charged ions are selectively removed from the electrically neutral chitin oligomers in the diluate circuit. The longer the fluids are pumped through the stack, the better is the desalination of the diluate. Preferred membranes provide transference numbers ranging from 0.9 to 0.98, and display very low electrical resistance, usually ranging from 2–4 Ohm/cm$^2$. Since the membrane resistance decreases with an increase in temperature, temperatures of 20° to 40° C. are preferred operational temperatures during the electrodialysis process. The electrodialyzed oligomers may optionally be further concentrated by, e.g., standard lyophilization procedures. If lyophilization is performed, prior to step IV the lyophilized chitin hydrolysate is redissolved in an appropriate volume of $H_2O$.

In a preferred embodiment of step IV, chitin oligomers are purified from desalted reaction mixtures by gel filtration. Preferred, non-limiting examples of gel filtration matrices are dextrans, agarose beads, and polyacrylamide beads. In a more preferred embodiment, Bio-Gel P gels are used for purification of chitin oligomers from desalted reaction mixtures. Bio-Gel P gels are polyacrylamide beads for high resolution gel filtration. The gels are prepared by copolymerization of acrylamide and N,N'-methylene-bis-acrylamide. Due to their synthetic composition, Bio-Gel P gels do not support microbial growth or leach carbohydrates as dextrans and agarose gels can. Bio-Gel P gels are extremely hydrophilic and essentially free of charge. In a most preferred embodiment, Bio-Gel P-4 gels are used for purification of chitin oligomers from desalted reaction mixtures. Useful, non-limiting examples are medium Bio-Gel P-4 gels (particle size range of hydrated beads: 90–180 µm) and fine Bio-Gel P-4 gels (particle size range of hydrated beads: 45–90 µm). Both gels offer a comparable molecular weight fractionation range (approximately 800–4000 Da). Typical flow rates are 15–20 cm$^3$/hour for the medium gel and 10–15 cm$^3$/hour for the fine gel.

In another preferred embodiment of step IV, chitin oligomers are purified by preparative HPLC procedures including gel filtration HPLC and reverse-phase HPLC.

In yet another preferred embodiment of step IV, higher chitin oligomers, preferably hexameric to decameric chitin oligomers, are separated from monomeric N-acetylglucosamine and lower chitin oligomers, preferably dimeric to pentameric chitin oligomers, by precipitation in the presence of salt, e.g., in the presence of ammonium sulfate as described by Usui, T., Matsui, H., and Isobe, K. (Carbohydr. Res. 203:65–77, 1990), incorporated herein by reference.

In another preferred embodiment, a procedure for the predominant production of water-soluble tetrameric to heptameric chitin oligomers (method B) is comprised of the following four steps:

(I) fragmentation of chitin to particles with a mean diameter of 120 µm or less;

(II) partial hydrolysis of the fragmented chitin in a concentrated hydrohalogenic acid;

(III) desalination of neutralized chitin hydrolysates by flow filtration; and (IV) separation of desalted chitin oligomers, e.g., by Bio-Gel P-4 gel filtration.

Method B differs from method A by the procedure used for desalination of neutralized chitin hydrolysates. In method B, desalination is accomplished by flow filtration techniques. Although flow filtration techniques require more time for the desalination processes than electrodialysis procedures, they provide an unexpected advantage since they allow desalination and removal of non-desired monomeric N-acetylglucosamine residues and dimeric and trimeric chitin oligomers in a single step. Using membranes of appropriate pore size, only a small percentage of tetrameric, pentameric, and hexameric chitin oligomers pass through the membrane, whereas higher oligomers do not pass through the membrane at all, thus desalination is accomplished with retention of the higher chitin oligomers. In one preferred embodiment, neutralized reaction mixtures are desalted by tangential flow filtration techniques. Preferred filtration rates, filters, filter areas, pump capabilities, and pump pressure capabilities are dependent on the production scale, and would be apparent to one skilled in the art. Tangential flow filtration processes may range from 0.5 l/hour to over 500 l/hour. Preferred, non-limiting examples of tangential flow filtration systems provide a filter area of approximately 1 m$^2$ for a filtration rate of 100 l/hour. Preferred pump capabilities and pump pressure capabilities are adjusted to required filtration volumes. For example, a pump capability of 4 l/min and a pump pressure capability of 2 bar (30 psi) is preferred for a filtration rate of up to 30 l/hour, whereas for a filtration rate of up to 150 l/hour a pump capability of 16 l/hour and a pump pressure capability of 7 bar (100 psi) is preferred. Preferred, non-limiting examples of membranes for tangential flow filtration include polymer membranes. Especially useful are membranes with a molecular weight cut-off in the range of 1000 Da and less which allow for a simultaneous selective removal of non-desired N-acetylglucosamine, dimeric and trimeric chitin oligomers.

In another aspect of this embodiment, ceramic membrane filters are used for desalination of neutralized chitin hydrolysates by flow filtration. Since ceramic membrane filters are highly resistant against high pressure, they are especially suitable for industrial production processes.

In another preferred embodiment, methods A and B are combined in a procedure for the production of water-soluble tetrameric to decameric chitin oligomers (method C). This procedure is comprised of the following five steps:

(I) fragmentation of chitin to particles with a mean diameter of 120 µm or less (as described above for method A);

(II) partial hydrolysis of the fragmented chitin in concentrated hydrochloric (or other hydrohalogenic) acid (as described above for method A);

(III) desalination of neutralized chitin hydrolysates by electrodialysis (as described above for method A); and (IV) selective removal of monomeric N-acetylglucosamine and dimeric and trimeric chitin oligomers by flow filtration (as described above for method B).

(V) separation of desalted chitin oligomers, e.g., by Bio-Gel P-4 gel filtration (as described for method A).

The invention will be further described by reference to the following examples, which are not intended to limit the present invention.

EXAMPLES

EXAMPLE 1. FRAGMENTATION OF CHITIN

Figure 2:
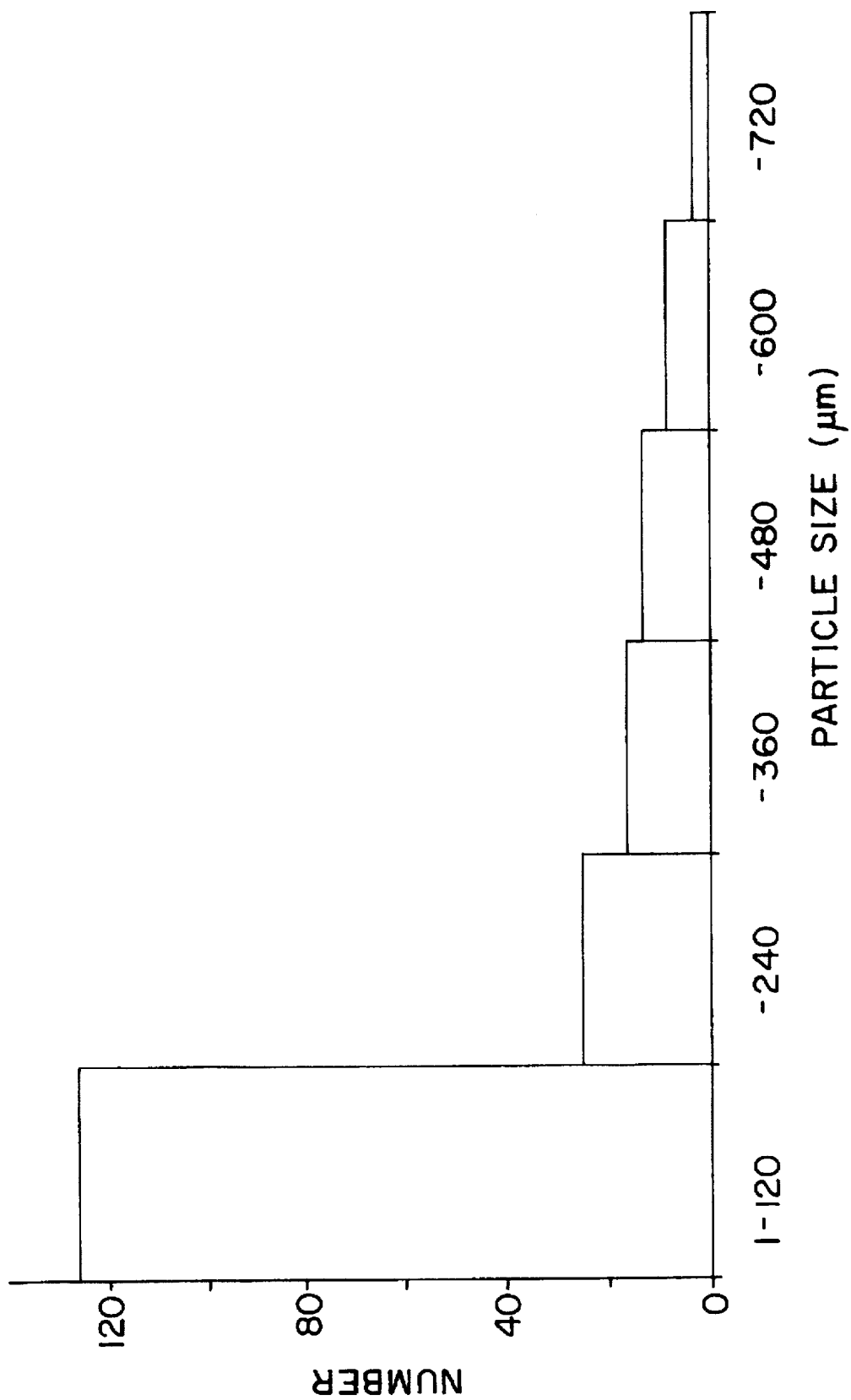
FIG. 2. Mean particle size of fragmented chitin after treatment with a hammer mill equipped with a double-sided swing beater system. Experimental details are described in Example 1.
Figure 3:
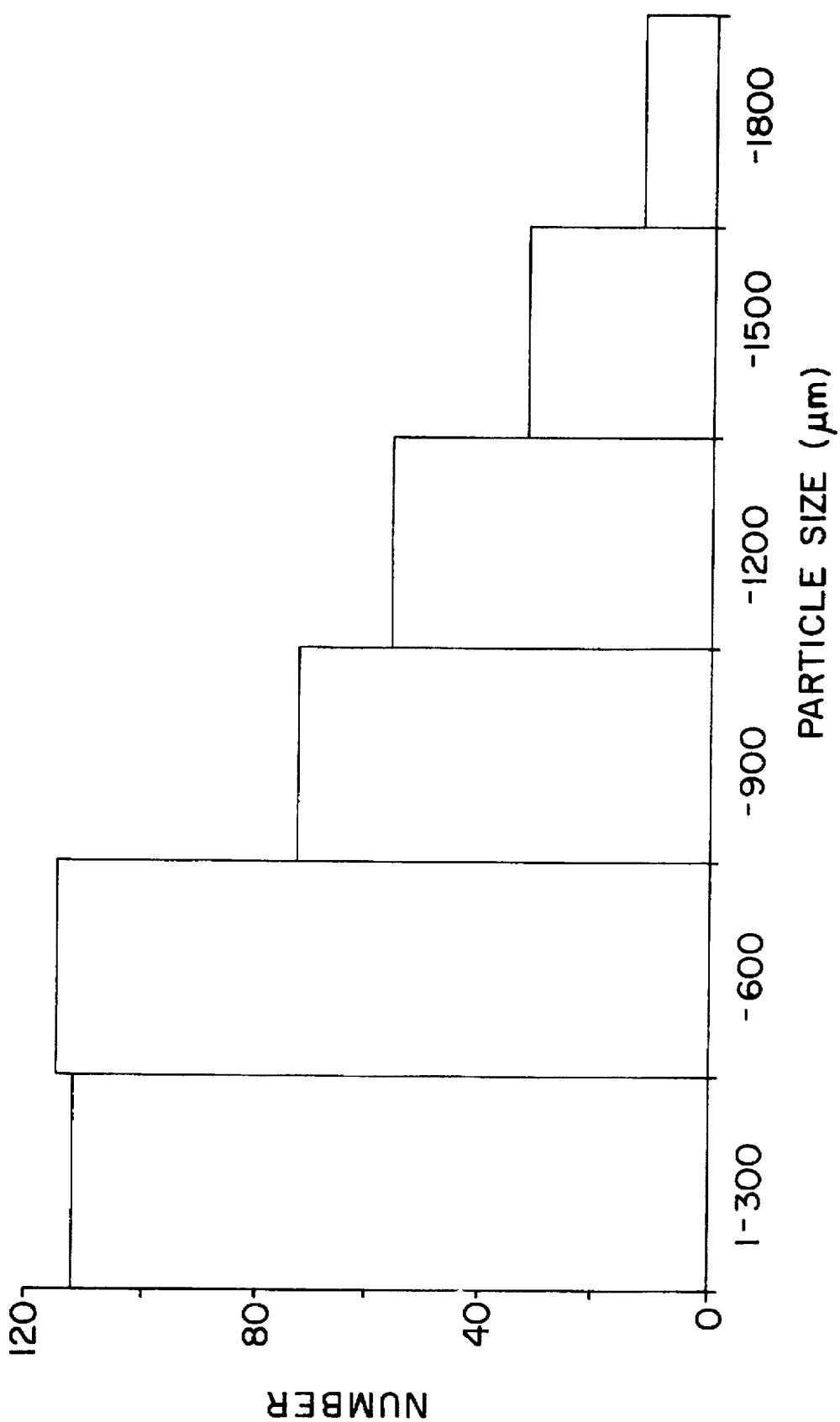
FIG. 3. Particle size of fragmented chitin without mill treatment.

Chitin obtained from crab shells (Sigma Chemical Co., St. Louis, Mo.; flakes, practical grade) is fragmented to superfine particles by treatment with a hammer mill equipped with a double-sided swing beater system and a baffle-ribbed grinding track (Multi-Purpose Mill 25 MZ, Hosokawa Alpine AG, Augsburg, Germany). Using this novel procedure, 100 g chitin requires less than 5 minutes to be converted to chitin particles with a diameter of 120 µm or less (FIG. 2). Without mill treatment, chitin particles are approximately 5–10 times larger (FIGS. 3).

EXAMPLE 2. PARTIAL HYDROLYSIS OF FRAGMENTED CHITIN IN CONCENTRATED HCl

The super-finely ground chitin particles (100 g) obtained by the mill treatment described in Example 1, are dissolved with the aid of a mechanical stirrer in 400 ml of 12.5M HCl (250 mg chitin/ml HCl) in a 1 liter three-necked flask. After stirring for 10 minutes at 20° C., the solution is incubated for another 110 minutes at 40° C. with continuous stirring. During the incubation, the viscosity of the solution decreases significantly and a deep brown color develops. Prior to neutralization the reaction mixture is transferred into a 4 liter Pyrex round-bottom boiling flask with a standard taper and placed into a water bath containing an ice/salt mixture. After cooling for a few minutes, 400 ml of an ice-cold 50% aqueous sodium hydroxide solution is carefully added to the continuously stirred reaction mixture. The addition of the sodium hydroxide solution is extended over a period of 20 minutes to keep the temperature always below 25° C. After neutralization, insoluble material is removed from the chitin hydrolysate by centrifugation or filtration. The insoluble material is washed, dried and weighed to determine the extent of hydrolysis of chitin.

EXAMPLE 3. ELECTRODIALYSIS OF NEUTRALIZED CHITIN HYDROLYSATES

Figure 4:
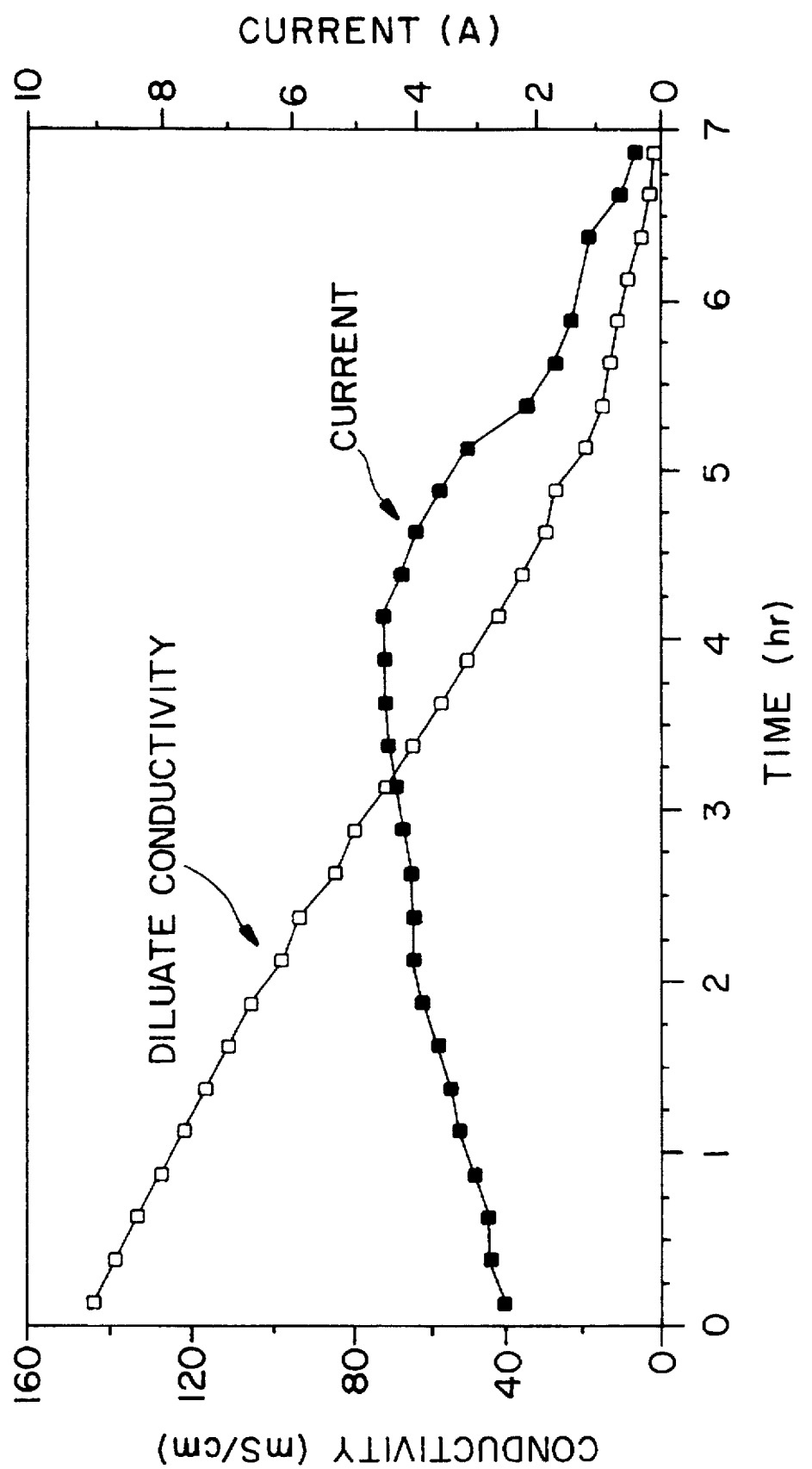
FIG. 4. Desalination of neutralized chitin hydrolysates by electrodialysis. Experimental details are described in Example 3.

Prior to desalination by electrodialysis, the neutralized chitin hydrolysate (6 liters) containing 20 moles NaCl is adjusted to pH 7.0. The solution has a density (d) of 1.1 and a conductivity of 164.6 mS/cm. The electrodialysis system is equipped with stacks of 10 anion exchange (ACS) membranes and 12 cation exchange (CMS) membranes. In the diluate circuit the membrane distance is adjusted to 0.75 mm, and in the concentrate circuit to 0.5 mm. The rinsing circuit for the electrodes (Ti-electrodes) of the system is filled with 0.1% $Na_2SO_4$. During the electrodialysis process, the pH of the diluate is continuously monitored and maintained at pH 7 by the addition of 1 N NaOH. The conductivity of the concentrate is also continuously monitored during the electrodialysis process and maintained at 100 mS/cm by partial removal of concentrate with a higher conductivity and replacement of the removed volume with water. The temperature of the system is kept at 30° C. With a potential difference of 20 V applied across the cell, desalting is completed within six to seven hours. At this point, the initial current of 4.64 A has dropped to 0.8 A (FIG. 4). The residual level of NaCl in such desalinated chitin hydrolysates is below the detection level with silver nitrate (FIG. 5). Using method A for the production of chitin oligomers, chitin hydrolysates are lyophilized after completion of desalination. Using method C, the desalinated chitin hydrolysates are subjected to flow filtration without prior lyophilization.

EXAMPLE 4. TANGENTIAL FLOW FILTRATION OF NEUTRALIZED CHITIN HYDROLYSATES

Figure 8:
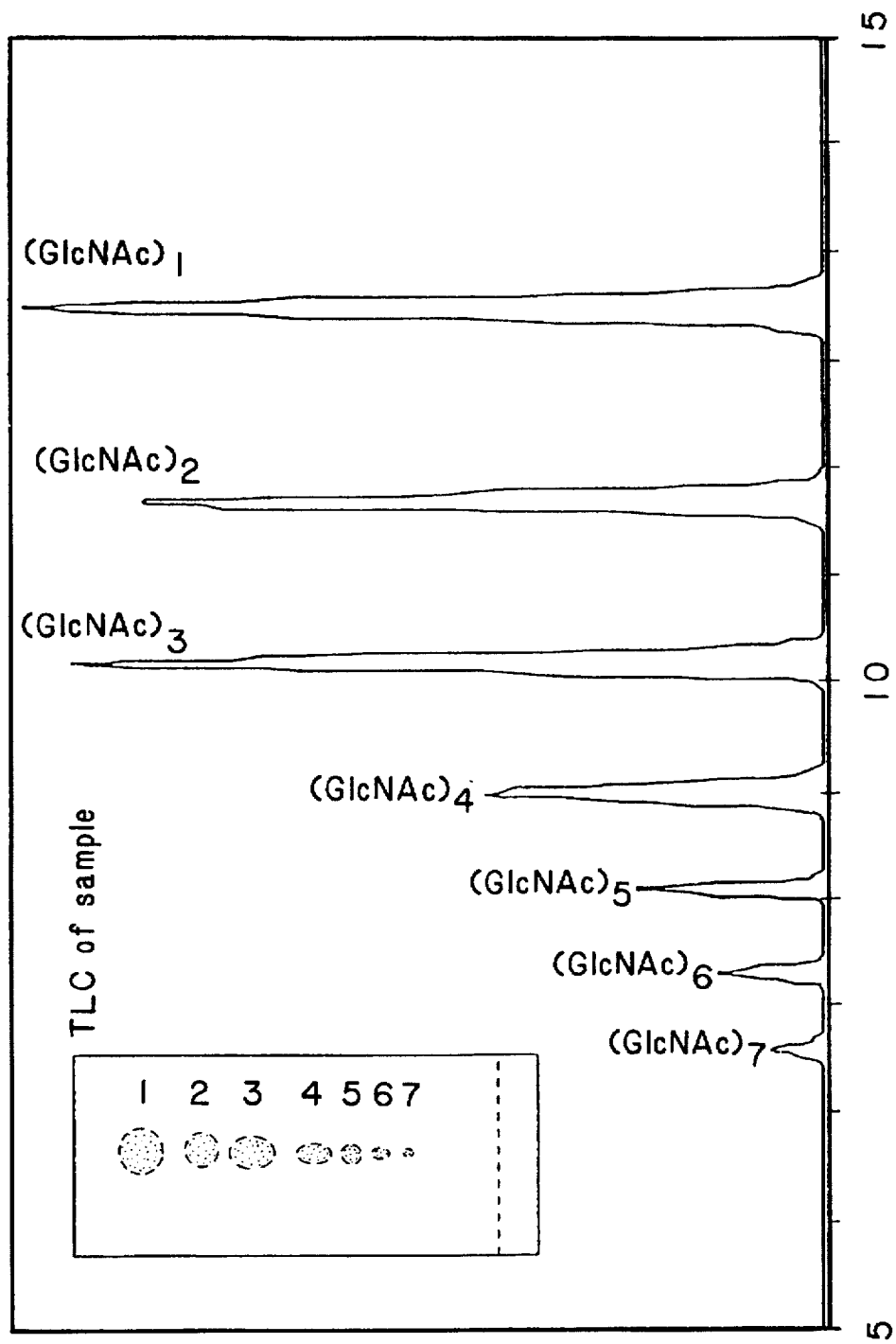
FIG. 8. Removal of N-acetylglucosamine, dimeric and trimeric chitin oligomers from neutralized chitin hydrolysates by tangential flow filtration. Experimental details are described in Examples 4 and 5. The inset shows a TLC analysis of the permeate fraction (obtained by tangential flow filtration of a neutralized chitin hydrolysate) before Bio-Gel P-4 chromatography. The position of N-acetylglucosamine and dimeric to heptameric chitin oligomers are indicated by the numbers 1–7.

According to method B, a neutralized chitin hydrolysate (1.5 liter) containing 5 moles NaCl is loaded into a tangential flow filter cassette equipped with a 1 kDa cut-off membrane (Filtron Ultrasette, Millipore Intertech, Bedford, Mass.). Using a pressure of 0.5 bar, the starting volume of 1.5 liters is reduced to 0.75 liters (concentrate fraction) after 48 hours. Accordingly, the NaCl content in the concentrate fraction is reduced by approximately 50% (2.6 mol/0.75 liters) (FIG. 9). Concomitantly, the content of monomeric N-acetylglucosamine, dimeric and trimeric chitin oligomers in the concentrate fraction is significantly reduced as revealed by chromatographic analysis of the permeate fraction (0.75 liters) by Bio-Gel P-4 gel filtration (see Example 5). FIG. 8 shows that mainly monomers, dimers and trimers are removed by tangential flow filtration, while tetrameric to hexameric chitin oligomers are too large to pass the membrane in larger quantities. After completion of the filtration process, both the concentrate fraction and the permeate fraction are lyophilized yielding 54 g of concentrate and 14 g of permeate.

EXAMPLE 5. BIO-GEL P-4 CHROMATOGRAPHY OF DESALTED CHITIN HYDROLYSATES

Figure 6:
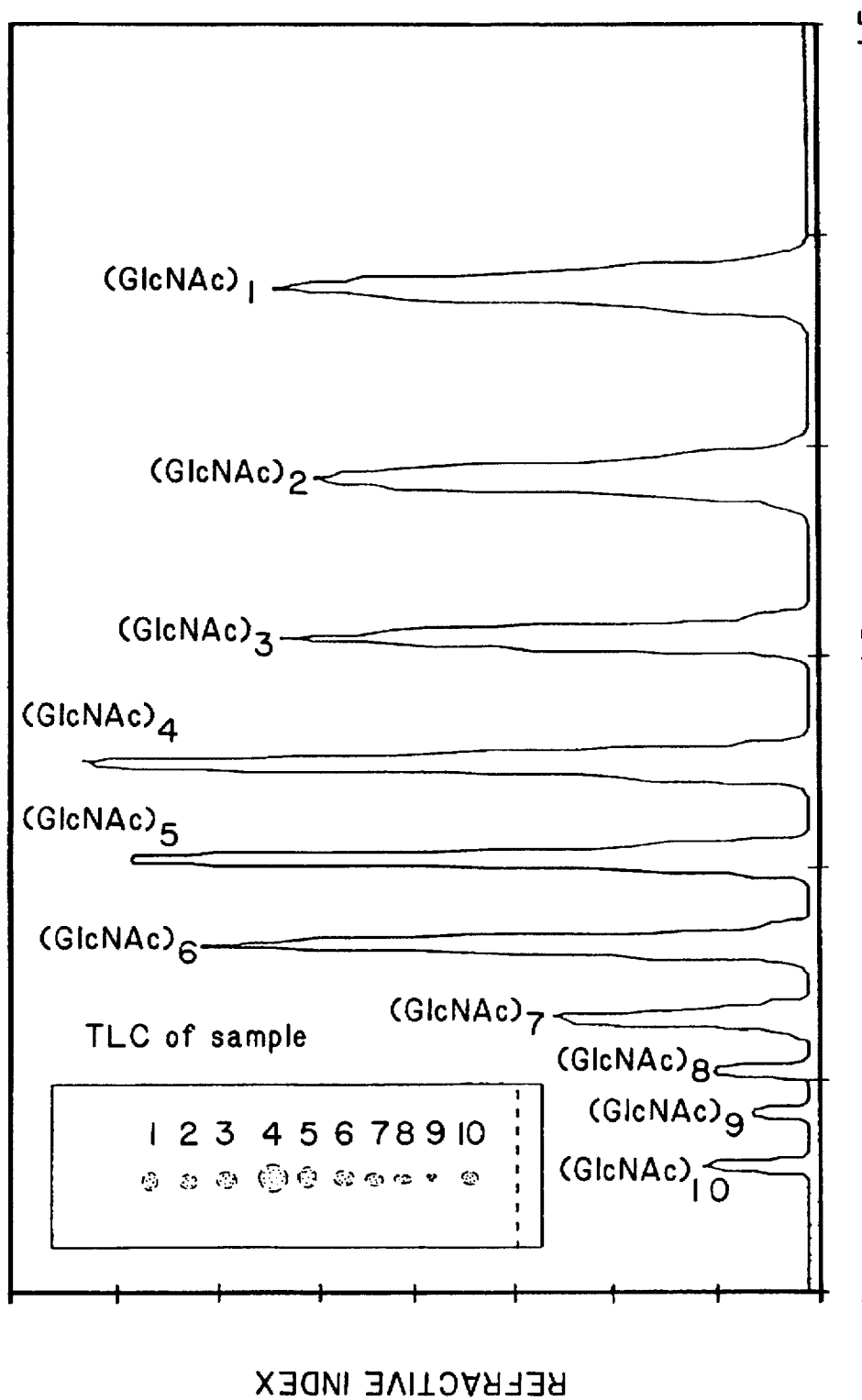
FIG. 6. Bio-Gel P-4 chromatography of a neutralized chitin hydrolysate after electrodialysis. Experimental details are described in Example 5. The inset shows a TLC analysis of the desalinated chitin hydrolysate before Bio-Gel P-4 chromatography. The positions of N-acetylglucosamine and dimeric to decameric chitin oligomers are indicated by the numbers 1–10.

Bio-Gel P-4 (200–400 mesh) is allowed to swell in distilled water for 4 hours at room temperature and is then degased. After pouring the gel slurry (4.2 liters) into the column (1.5 m×6 cm), the column is washed with approximately 4 column volumes of water. Samples of 40 ml of water (bidest) containing 3 g of desalted chitin hydrolysate (method A: chitin hydrolysate after electrodialysis; method B: chitin hydrolysate after flow filtration; method C: chitin hydrolysate after electrodialysis and subsequent flow filtration) are used for each fractionation performed at a flow rate of 4.75 ml/min over a period of approximately 14 hours (FIG. 6). Eluted chitin oligomers are continuously monitored by refractive index analysis. Fractions (20 ml) containing chitin oligomers of the same lengths are combined and lyophilized.

EXAMPLE 6. ANALYSIS OF CHITIN OLIGOMERS BY TLC

The analysis of chitin oligomers by thin layer chromatography (TLC) is performed on silica plates 60 $GF_{254}$ (Merck, Darmstadt, Germany) using 2-propanol/water/$(NH_4)_2SO_4$ (72:27:1) as solvent. Separated chitin oligomers are detected by spraying the plate with a mixture of sulfuric acid, ethanol, and water followed by heating for a few minutes.

EXAMPLE 7. ANALYSIS OF CHITIN OLIGOMERS BY HPLC

Purified chitin-oligomers are analyzed by HPLC on a Radial-PAK µBondapak $NH_2$ column (Waters Associates). The elution is carried out with an acetonitrile-water mixture (70:30) as described by Izume, M., Nagae, S., Kaagishi, H., and Ohtakara, A. (Biosci. Biotech. Biochem. 56:1327–1328, 1992). The absorbance is monitored at 210 nm.

EXAMPLE 8. ANALYSIS OF PURIFIED CHITIN-OLIGOMERS BY MASS SPECTROMETRY

Prior to analysis by mass spectrometry, the purity of chitin-oligomers obtained from Bio-Gel P-4 chromatography is confirmed by HPLC analysis as described in Example 7.

We claim:
1. A process for the production of water-soluble chitin oligomers comprising the steps of:
   (a) fragmenting chitin to particles with a mean diameter of 120 µm or less;
   (b) mixing the chitin particles with a concentrated hydrohalogen acid solution to achieve partial hydrolysis;
   (c) neutralizing the reaction mixture to limit the hydrolysis of the chitin particles;
   (d) desalinating the neutralized chitin hydrolysates from step (c) by a method selected from the group consisting of: (1) electrodialysis, wherein the number of membranes used is proportional to the salt content of the diluate; and (2) flow filtration using a ceramic membrane; and
   (e) separating the desalted chitin oligomers from the desalted reaction mixture of step (d).
2. The process of claim 1, wherein the chitin oligomers produced have the general formula:

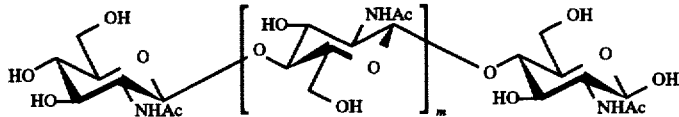

wherein m=0–8.

3. The process of claim 2, wherein m=4–8.

4. The process of claim 1, wherein in step (a) the chitin is fragmented to particles having a mean diameter of 120 µm or less by processing the chitin in a mill equipped with one or more beater systems.

5. The process of claim 1, wherein the chitin particles with a diameter of 120 µm or less are fragmented to particles having a mean diameter of about 10 to 50 µm by processing the chitin particles in a fine impact mill or zig zag classifier.

6. The process of claim 1, wherein the chitin particles with a mean diameter of 10–50 µm are fragmented to ultrafine particles having mean diameters of less than 10 μm by processing the chitin particles in an airstress ultrafine classifier.

7. The process of claim 1, wherein in step (b) the chitin particles are dissolved in a concentrated hydrohalogenic acid and subjected to partial hydrolysis at elevated temperatures.

8. The process of claim 7, wherein the concentrated hydrohalogenic acid is 12.5M HCl.

9. The process of claim 7, wherein the chitin particles are dissolved in the acid using a mechanical stirrer at a concentration of 200 to 400 mg chitin particles per ml concentrated hydrohalogenic acid.

10. The process of claim 7, wherein the hydrolysis reaction is carried out at a temperature between 20° C. and 45° C. for a period of 100 to 150 minutes with continuous stirring.

11. The process of claim 10, wherein the temperature is 40° C.

12. The process of claim 1, wherein in step C the neutralization is effected by the addition of ice-cold 50% sodium or potassium hydroxide solution under conditions that keep the temperature of the chitin hydrolysate below 25° C.

13. The process of claim 1, wherein in step (d) the neutralized chitin hydrolysate is filtered to remove insoluble material and is desalinated to a salt concentration of less than 0.1 g/l by electrodialysis.

14. The process of claim 13, wherein desalination is performed by electrodialysis, during which the pH of the desalted fraction is maintained at approximately pH 7.

15. The process of claim 13, wherein desalination is performed by electrodialysis, during which the conductivity of the concentrate is maintained at approximately 100 mS/cm.

16. The process of claim 13, wherein desalination is performed by electrodialysis, during which the temperature is kept at a temperature ranging from about 20° C. to 40° C.

17. The process of claim 1, wherein following step (d) the desalinated hydrolysate is lyophilized.

18. The process of claim 17, wherein the lyophilized chitin hydrolysate is redissolved in water and subjected to the separation process of step (e), which comprises a process that will separate individual chitin oligomers of defined length into individual fractions or groups of chitin oligomers of different lengths within defined ranges into individual fractions.

19. The process of claim 18, wherein the lyophilized chitin hydrolysate is redissolved in water at a concentration of about 2 to 4 g of solid per 40 ml of water.

20. The process of claim 18, wherein the separation of individual chitin oligomers of defined length is accomplished by a chromatographic procedure selected from the group consisting of low pressure gel filtration, high pressure gel filtration and reverse-phase HPLC.

21. The process of claim 18, wherein the separation of groups of chitin oligomers of different lengths is accomplished by salt precipitation of higher chitin oligomers.

22. The process of claim 1, wherein in step (d) the neutralized chitin hydrolysate is filtered to remove insoluble material, and is thereafter desalinated by flow filtration.

23. The process of claim 22, wherein the desalination is effected by tangential flow filtration.

24. The process of claim 23, wherein the tangential flow filtration is performed with membranes having a molecular weight cut-off of 1 KDa or less, whereby salt and dimeric and trimeric chitin oligomers from the chitin hydrolysate are removed and the higher chitin oligomers in the desalinated fraction are enriched.

25. The process of claim 23, wherein the filtration rate ranges from 0.5 L/hour to about 500 L/hour.

26. The process of claim 22, wherein the desalination is effected by flow filtration through a ceramic membrane.

27. The process of claim 26, wherein ceramic membrane filters with pore sizes of about 5 nm to 1 nm are used for desalination and for the removal of lower chitin oligomers from the chitin hydrolysate.

28. The process of claim 1, wherein the chitin hydrolysates, desalinated by flow filtration, are lyophilized.

29. The process of claim 28, wherein the lyophilized chitin hydrolysate is redissolved in water and subjected to the separation process of step (e), which comprises a process that will separate individual chitin oligomers of defined length into individual fractions or groups of chitin oligomers with different lengths within defined ranges into individual fractions.

30. The process of claim 29, wherein the lyophilized chitin hydrolysate is redissolved in water at a concentration of about 2 to 4 g solid per 40 ml of water.

31. The process of claim 28, wherein the separation of individual chitin oligomers of defined length is accomplished by a chromatographic procedure selected from the group consisting of low pressure gel filtration, high pressure gel filtration and reverse-phase HPLC.

32. The process of claim 28, wherein the separation of groups of chitin oligomers of different lengths is accomplished by salt precipitation of higher chitin oligomers.

33. The process of claim 1, wherein after neutralization the chitin hydrolysates are filtered, and are thereafter desalinated by electrodialysis and subsequently subjected to flow filtration without prior lyophilization.

34. The process of claim 33, wherein the neutralized and filtered chitin hydrolysates are desalinated by electrodialysis and subsequently subjected to flow filtration without prior lyophilization, wherein in step (d) the neutralized chitin hydrolysate is desalinated to a salt concentration of less than 0.1 g/l by electrodialysis.

35. The process of claim 34, wherein desalination is performed by electrodialysis, during which the pH of the desalted fraction is maintained at approximately pH 7.

36. The process of claim 34, wherein desalination is performed by electrodialysis, during which the conductivity of the concentrate is maintained at approximately 100 mS/cm.

37. The process of claim 34, wherein desalination is performed by electrodialysis, during which the temperature is kept at a temperature ranging from about 20° C. to 40° C.

38. The process of claim 33, wherein the desalination is effected by tangential flow filtration.

39. The process of claim 38, wherein the tangential flow filtration is performed with membranes having a molecular weight cut-off of 1 KDa or less, whereby salt and dimeric and trimeric chitin oligomers from the chitin hydrolysate are removed and the higher chitin oligomers in the desalinated fraction are enriched.

40. The process of claim 38, wherein the filtration rate ranges from 0.5 L/hour to about 500 L/hour.

41. The process of claim 38, wherein the desalination is effected by flow filtration through a ceramic membrane.

42. The process of claim 38, wherein ceramic membrane filters with pore sizes of about 5 nm to 1 mm are used for the removal of lower chitin oligomers from the chitin hydrolysate.

43. The process of claim 1, wherein the chitin hydrolysate, desalinated by electrodialysis and subsequently subjected to flow filtration, is lyophilized.

44. The process of claim 43, wherein the lyophilized chitin hydrolysate is redissolved in water and subjected to the separation process of step (e), which comprises a process that will separate individual chitin oligomers of defined length into individual fractions or groups of chitin oligomers with different lengths within defined ranges into individual fractions.

45. The process of claim 44, wherein the lyophilized chitin hydrolysate is redissolved in water at a concentration of about 2 to 4 g solid per 40 ml of water.

46. The process of claim 44, wherein the separation of individual chitin oligomers of defined length is accomplished by a chromatographic procedure selected from the group consisting of low pressure gel filtration, high pressure gel filtration and reverse-phase HPLC.

47. The process of claim 44, wherein the separation of groups of chitin oligomers of different lengths is accomplished by salt precipitation of higher chitin oligomers.

48. The process of claim 1, wherein di-N-acetylchitobiose is obtained at a yield of 8.6±2.3 g per 100 g chitin.

49. The process of claim 1, wherein tri-N-acetylchiotriose is obtained at a yield of about 8.9±2.4 g per 100 chitin.

50. The process of claim 1, wherein tetra-N-acetylchitotetraose is obtained at a yield of about 8.7±2.3 g per 100 g chitin.

51. The process of claim 1, wherein penta-N-acetylchitopentaose is obtained at a yield of about 8.1±2.1 g per 100 g chitin.

52. The process of claim 1, wherein hexa-N-acetylchitohexaose is obtained at a yield of about 3.6±0.7 g per 100 g chitin.

53. The process of claim 1, wherein hepta-N-acetylchitoheptaose is obtained at a yield of about 1.0±0.4 g per 100 g chitin.

54. The process of claim 1, wherein octa-N-acetylchitooctaose is obtained at a yield of about 0.3±0.2 g per 100 g chitin.

55. The process of claim 1, wherein nona-N-acetylchitononaose is obtained at a yield of about 0.2±0.1 g per 100 g chitin.

56. The process of claim 1, wherein deca-N-acetylchitodecaose is obtained at a yield of about 0.3±0.2 g per 100 g chitin.

* * * * *